United States Patent
Lepage et al.

(10) Patent No.: US 9,523,660 B2
(45) Date of Patent: Dec. 20, 2016

(54) METHOD OF CONDUCTING PROBE COUPLING CALIBRATION IN A GUIDED-WAVE INSPECTION INSTRUMENT

(71) Applicants: Benoit Lepage, Ancienne-Lorette (CA); Guillaume Painchaud-April, L'Ancienne-Lorette (CA)

(72) Inventors: Benoit Lepage, Ancienne-Lorette (CA); Guillaume Painchaud-April, L'Ancienne-Lorette (CA)

(73) Assignee: OLYMPUS SCIENTIFIC SOLUTIONS AMERICAS INC., Waltham, MA (US)

( * ) Notice: Subject to any disclaimer, the term of this patent is extended or adjusted under 35 U.S.C. 154(b) by 128 days.

(21) Appl. No.: 14/674,988

(22) Filed: Mar. 31, 2015

(65) Prior Publication Data
US 2016/0290972 A1 Oct. 6, 2016

(51) Int. Cl.
G01N 29/30 (2006.01)
G01N 29/07 (2006.01)
G01N 29/28 (2006.01)

(52) U.S. Cl.
CPC .............. *G01N 29/30* (2013.01); *G01N 29/07* (2013.01); *G01N 29/28* (2013.01); *G01N 2291/262* (2013.01)

(58) Field of Classification Search
CPC ........ G01N 29/30; G01N 29/07; G01N 29/28; G01N 2291/262
USPC .............. 73/1.79, 1.81, 1.82, 622, 624, 625, 73/627–629; 702/97, 103
See application file for complete search history.

(56) References Cited

U.S. PATENT DOCUMENTS

| | | | | |
|---|---|---|---|---|
| 4,462,082 A | * | 7/1984 | Thiele | G01N 29/4463 367/13 |
| 5,719,538 A | * | 2/1998 | Kadota | H03H 9/02551 310/313 A |
| 7,997,139 B2 | * | 8/2011 | Owens | G01N 29/2412 702/39 |
| 8,002,704 B2 | | 8/2011 | Torp et al. | |
| 8,577,629 B2 | | 11/2013 | Simard et al. | |
| 2013/0194891 A1 | | 8/2013 | Kristoffersen et al. | |
| 2013/0263667 A1 | * | 10/2013 | Volker | G01B 17/02 73/598 |

\* cited by examiner

*Primary Examiner* — Hezron E Williams
*Assistant Examiner* — Marrit Eyassu
(74) *Attorney, Agent, or Firm* — C. Tricia Liu

(57) ABSTRACT

The method for calibrating an inspection instrument coupled with acoustic transducers disposed at circumferential positions distributed around a surface of an elongated object to inspect generally has the steps of: for each one of the circumferential positions, measuring a first and a second received signal using two acoustic transducers disposed at two axial positions along the object, the received signals resulting from the propagation of an acoustic guided wave signal along the object; identifying an acoustic mode according to the first received and the second received signals using a known period of time associated with the propagation of the acoustic guided wave signal between the two axial positions along the object; and determining a coupling coefficient associated with the acoustic mode, the coupling coefficient being indicative of the coupling of the acoustic transducers on the object; and calibrating the inspection instrument coupled to the object based on the coupling coefficients.

20 Claims, 6 Drawing Sheets

METHOD OF CONDUCTING PROBE COUPLING CALIBRATION IN A GUIDED-WAVE INSPECTION INSTRUMENT

FIELD OF THE INVENTION

This invention relates to the calibration of long range non-destructive testing and inspection systems (NDT/NDI) using acoustic guided modes propagating in elongated test objects. This invention is especially concerned with the calibration of portable guided wave inspection instruments that, when coupled with the elongated test object, relay acoustic waves from the transducer to the test object, and conversely from the test object to the transducer.

BACKGROUND OF THE INVENTION

The use of acoustic guided waves is a promising way to screen corrosion and general wall thinning in elongated test objects such as pipelines. The capacity to assess structural integrity several meters at a time in an elongated structure offers opportunities to decrease inspection costs by pinpointing specific areas of concern. Acoustic guided waves enable a more thorough evaluation of structures with respect to conventional NDT/NDI means spot checks based on historical knowledge or random sampling, which can lead to an increase in overall structure safety, for instance.

Amongst the many possible inspection instruments enabling guided wave inspection, one is a portable probe assembly that may be reused at multiple axial positions along a pipe structure. When properly mounted on a pipe to be inspected, a probe assembly of the inspection instrument is fixed along the circumference of the pipe with acoustically sensitive transducers uniformly distributed along the circumference of the probe assembly, at a plurality of circumferential positions, and facing the exterior of the test object, see U.S. Pat. No. 7,997,139 B2 for instance.

When using such a probe assembly, the acoustic transducers (e.g. piezoelectric transducers) can be dry coupled with the test object by applying a normal force against the exterior of the test object. This may be achieved, for instance, by pneumatic or hydraulic means (e.g. inflating a bladder behind the transducers), or applying a tensile force along the probe assembly.

A satisfactory guided wave inspection instrument should rely on the circumferentially uniform correspondence between the circulating acoustic wave in the pipe structure and the detected wave perceived by the transducers. In other words, the amplitude level detected by the transducers, or groups of transducers, should be proportional in a constant way over the complete circumference of the test object to the circulating acoustic wave amplitude. However, the coupling between the transducers of such inspection instruments and the elongated structure is often non-uniform.

Although existing inspection methods, inspection instruments, and systems involving guided-wave have been satisfactory to a certain degree, there remained room for improvement, test particularly in terms of providing guided wave inspection instruments which avoid the problem of non-uniform coupling between the transducers, or groups of transducers, and an elongated and/or cylindrical test object. Such guided wave inspection instruments could be useful especially given that the non-uniformity may change from one installation to another due to the changing conditions of the surface of the elongated test objects and on the individual transducer positioning relative to the surface of the elongated test object.

Other inventions address the problem of the non-uniform sensitivity of acoustic transducers. For instance, U.S. Pat. No. 8,002,704 addresses the problem of assessing a contact level between an array of transducers and a body through a frequency-based analysis together with a phased array beam. However, this method is not used for the calibration of the guided wave inspection instrument since the beam is formed of free propagating wave packets.

Other publications, such as U.S. Pat. No. 9,577,629 and US 2013/0194891, use averaging of inspection data (different observables may be defined) to provide per transducer element characteristic values. However, these values are compared from element to element to detect significant deviations from a standard acceptability criterion. Elements outside the acceptability range are deemed faulty and their sensitivity deviation may be compensated to equalize the array sensitivity level.

SUMMARY OF THE INVENTION

The invention presented in the current paper uses a pre-inspection stage to identify, using calibration data comprising received signal data, an acoustic guided mode enabling adequate calibration of an inspection instrument. The originality of the invention presented here stems from the direct use of the known properties of the acoustic guided mode to calibrate the guided wave inspection instrument. As mentioned above, the current invention aims at solving the problem of non-uniform coupling between a plurality of acoustic transducers of a probe assembly of the inspection instrument and an elongated test object.

Because of the intrinsic dispersive nature of guided modes, the interpretation of the acoustic modes of a received guided wave signal is needed to correctly identify its origin along the axis of the pipe (i.e. a reflector to be diagnosed located at a certain distance from the guided wave inspection instrument). This may rely on Fourier series expansion of the amplitude of the received signal amplitude on all acoustic transducers, or groups of transducers, along the pipe circumference and at a given time position. However, since the coupling with the test object may change from one transducer to another, all measured amplitudes can be systematically biased by many unknown factors. This in turn impacts the Fourier series decomposition and ultimately, the capacity to position and interpret structural defects in the received and/or reflected signals.

The current invention makes use of an acoustic guided mode having a constant amplitude wherein the transducers are coupled to the elongated test object at two axial positions for each one of a plurality of circumferential positions. At each of these positions, a corresponding transducer measures a received acoustic signal associated with the propagation of the acoustic guided mode along the elongated test object. By using a period of time corresponding to the time of flight of the propagation of the acoustic guided mode between each of the two axial positions, the methods and devices described herein help identify the acoustic guided mode in the measured acoustic signals and subsequently determine calibration coefficients associated with the transducers of each one of the circumferential positions. Once the calibration coefficients are determined, the methods and devices described herein help calibrating the inspection instrument based on the calibration coefficients which, in turn, allow for uniform coupling between the transducers and the elongated test object.

Once the guided wave inspection instrument is properly calibrated with regards to the calibration coefficients, one may proceed with normal inspection procedures, which may include further calibration steps.

Although the acoustic mode can be any mode which has a constant amplitude at each one of the circumferential positions of the transducers and has a constant phase velocity, the acoustic mode T(0,1), which is known in the guided-wave industry to be uniform over the complete circumference of the pipe, can be advantageous. In T(0,1), "T" stands for the torsional motion of the particles composing the cylindrical structure; "0" is the angular index and means that the amplitude along the angular coordinate is uniform (i.e. given a radial position in the pipe, there's no amplitude change as one moves along the angular position); "1" is the radial index and means that there's a single maximum of amplitude along the radial coordinates. Indeed, unlike some other guided wave modes that may exist in an acoustic wave guide, the T(0,1) mode is non-dispersive which means that its phase velocity remains constant over the complete frequency axis. Therefore, identifying the acoustic T(0,1) mode from the received acoustic signals along the circumference of the pipe can provide a way to quantify coupling related deviations that may occur using the determined calibration coefficients.

Assuming reception and transmission associated with each one of the transducers are calibrated electronically, these calibration coefficients can be applied using a coupling calibrator to at least one of the transmission voltages and the reception gains of the corresponding transducer to equalize the instrument sensitivity over the circumference of the pipe.

The benefits of having uniform sensitivity over the circumference of the pipe are found on at least two main levels. On a first level, the received signals may now be expanded in normal modes with minimal coupling bias, thus improving the capacity of the guided wave inspection instrument to localize structural defects. Carrying out the calibration procedure for every new mechanical installation of the guided wave inspection instrument ensures the repeatability of the measured modes associated with a given reflector. On a second level, the transmitted signals may now be better controlled, thus enabling repeatable advanced "focus" forming techniques (such as the one presented in U.S. Pat. No. 7,997,139 B2) with dry coupled transducers.

Furthermore, the improved modal discrimination at the emission level can lead to a more energy efficient instrument because losses associated with the excitation of non-propagating modes otherwise unwillingly transmitted in the pipe by lack of knowledge of the coupling coefficients may now be minimized.

In accordance with an aspect, there is provided a method for calibrating an inspection instrument coupled with a plurality of acoustic transducers disposed at a plurality of circumferential positions distributed on a test surface of an elongated test object to be inspected, each of the acoustic transducers is acoustically coupled with the test surface during operation, the method comprising the steps of: for each one or one group of the plurality of circumferential positions, measuring at least a first and a second received signal using at least two or two groups of acoustic transducers disposed at two distinct axial positions along the elongated test object, the received signals resulting from the propagation of an acoustic guided wave signal along the elongated test object; identifying an acoustic mode according to the first received and the second received signals using a known period of time associated with the propagation of the acoustic guided wave signal between the two axial positions along the elongated test object; and determining a coupling coefficient associated with the acoustic mode, the coupling coefficient being indicative of the relative coupling condition between at least one of the at least two or two groups acoustic transducers and the elongated test object; and, calibrating the inspection instrument for the at least one of the at least two or two groups of acoustic transducers based on the plurality of coupling coefficients.

In accordance with another aspect, there is provided a coupling calibrator for calibrating an inspection instrument coupled with a plurality of acoustic transducers disposed at a plurality of circumferential positions distributed on a test surface of an elongated test object to be inspected, each of the acoustic transducers is acoustically coupled with the test surface during operation, the coupling calibrator comprising: a mode identifier configured to, for each one or one group of the plurality of circumferential positions, obtain at least a first and a second received signal being measured using at least two or two groups of acoustic transducers disposed at two distinct axial positions along the elongated test object, the received signals resulting from the propagation of an acoustic guided wave signal along the elongated test object; and identify an acoustic mode according to the first received and the second received signals using a known period of time associated with the propagation of the acoustic guided wave signal between the two axial positions along the elongated test object; a coupling calculator configured to determine a coupling coefficient associated with the acoustic mode for each one of the one or the one group of the plurality of circumferential positions, each of the coupling coefficients being indicative of the relative coupling condition between at least one of the two or the two groups of acoustic transducers and the elongated test object; and a coupling compensator configured to calibrate the inspection instrument for the at least one of the two or the two groups of acoustic transducers based on the plurality of coupling coefficients.

In accordance with another aspect, there is provided a guided wave inspection instrument for inspecting an elongated test object, the guided wave inspection instrument comprising: a probe assembly coupled with a plurality of acoustic transducers to be disposed at a plurality of circumferential positions distributed on a test surface of the elongated test object to be inspected, each of the acoustic transducers is acoustically coupled with the test surface during operation; an acquisition unit for receiving at least a first and a second received signal using at least two or two groups of acoustic transducers disposed at two distinct axial positions along the elongated test object, the received signals resulting from the propagation of an acoustic guided wave signal along the elongated test object; a memory for storing calibration data comprising the received signals; a processor coupled to the acquisition unit and to the memory, the processor further comprising a mode identifier configured to, for each one or one group of the plurality of circumferential positions, obtain at least a first and a second received signal being measured using at least two or two groups of acoustic transducers disposed at two distinct axial positions along the elongated test object, the received signals resulting from the propagation of an acoustic guided wave signal along the elongated test object; and identify an acoustic mode according to the first received and the second received signals using a known period of time associated with the propagation of the acoustic guided wave signal between the two axial positions along the elongated test object; a coupling calculator configured to determine a coupling coefficient associated with the acoustic mode for each one of the one or the one group of the plurality of circumferential positions, each of the coupling coefficients being indicative of the relative coupling condition between at least one of the two or the two groups of the plurality of the acoustic transducers and the elongated test object; and a coupling compensator configured to calibrate the guided wave inspection instrument for the at least one of the two or the two groups of acoustic transducers based on the plurality of coupling coefficients.

Many further features and combinations thereof concerning the present improvements will appear to those skilled in the art following a reading of the instant disclosure.

BRIEF DESCRIPTION OF THE OF THE DRAWINGS

In the figures.

Figure 4:
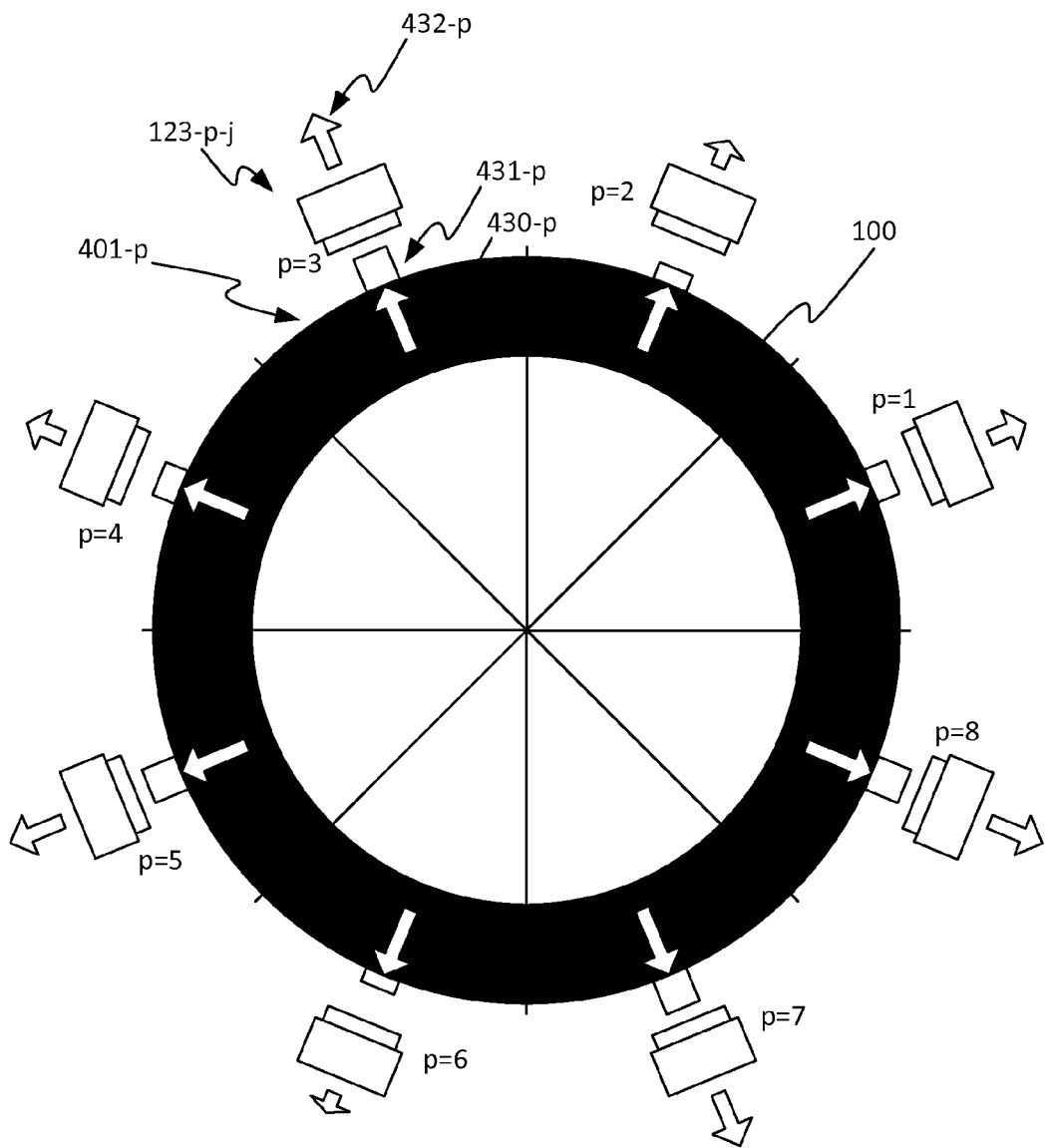
Figure 5:
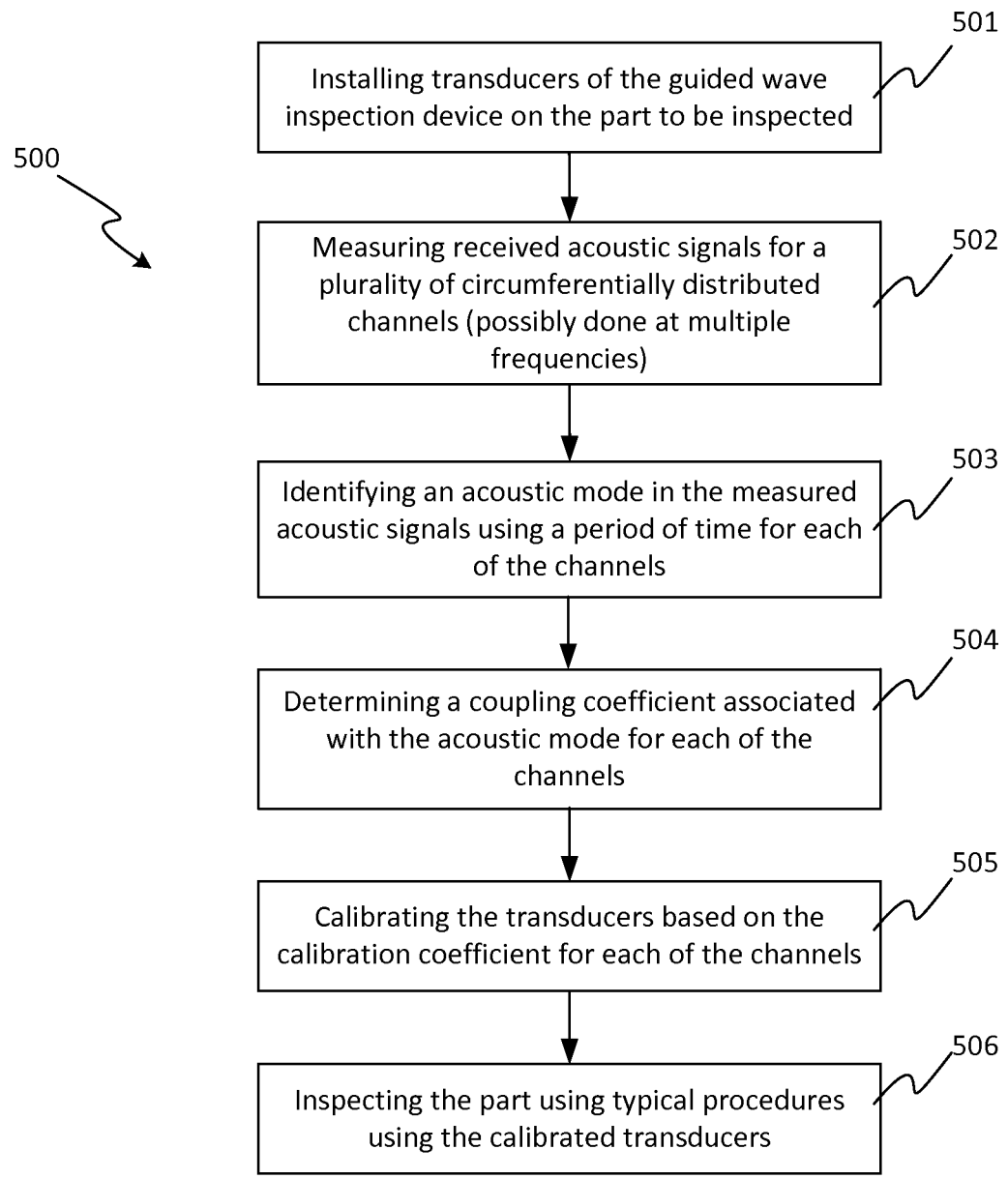

FIG. 4 is a cross-sectional view of a guided wave inspection instrument mounted on an elongated test object and showing a conceptual representation of the T(0,1) mode acoustic amplitude circulating in the test object, coupling level, and perceived T(0,1) mode amplitude by the transducers or groups of transducers, in accordance with one embodiment; and FIG. 5 is a flowchart of a method for calibrating a guided wave inspection instrument, in accordance with one embodiment.

These drawings depict exemplary embodiments for illustrative purposes, and variations, alternative configurations, alternative components and modifications may be made to these exemplary embodiments.

DETAILED DESCRIPTION OF THE INVENTION

This section provides further details on the invention, with reference to the drawing boards above.

The current invention applies to the calibration of a guided wave inspection instrument 120 comprising a probe assembly 124 with regards to its acoustic coupling with an elongated test object in which a guided wave can propagate. The elongated test object to be inspected typically has a test surface, typically provided in the form of a circular cross-section, on at least a portion of the elongated test object. For instance, the elongated test object may have a cylindrical shape which may or may not be constant along its length. In an embodiment, the elongated test object may have elbows or shoulders at some positions along its length.

Figure 1A:
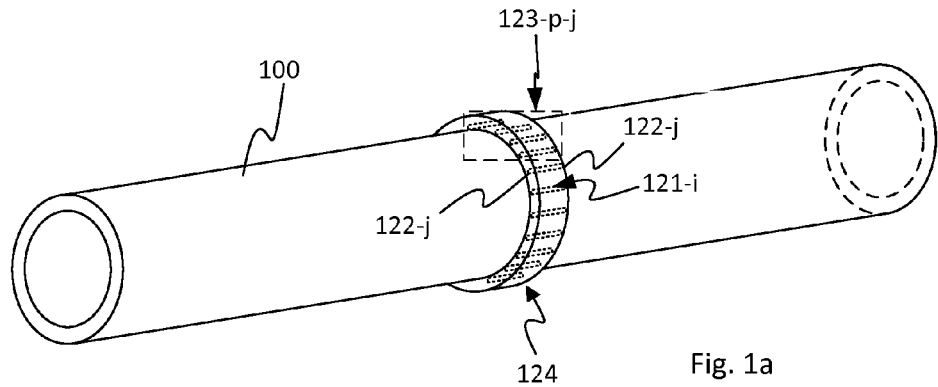
FIG. 1a is a schematic view of an example of a guided wave inspection instrument having transducers mounted on an elongated test object, in accordance with one embodiment.

FIG. 1a shows the physical appearance of the guided wave probe assembly 124 properly installed on a section of an elongated test object 100. The probe assembly 124 comprises acoustic transducers 122-$j$ for transmitting acoustic energy along the elongated test object as well as receiving acoustic energy from the elongated test object. For ease of reference, it is useful to define modules 121-$i$ of acoustic transducers and to define groups 123-$p$-$j$ of acoustic transducers wherein i denotes the circumferential position of the module 121-$i$, j denotes the axial position (or ring number) of the acoustic transducer 122-$j$ and that p denotes a set of circumferential positions incorporating more than one modules 121-$i$. wherein i, j and p are positive integers. The transducers may be excited at various frequencies to produce acoustic pulsed signals of prescribed spectral content (i.e. having a central frequency and a given bandwidth). In an embodiment, the modules are distributed evenly around the circular cross-section of the elongated test object. More details regarding the module 121-$i$ are presented herebelow in the description of FIG. 3a.

During use, the transducers 122-$j$ of the modules 121-$i$ are coupled with the elongated test object 100 so that acoustic energy can be shared between the modules 121-$i$ and the elongated test object 100. Such coupling may be provided in the form of dry-coupling, which consists of making physical contact between the modules and the test object. Such dry-coupling may involve any suitable means including pneumatic, hydraulic, and tensile means to force contact between the transducers and the elongated test object, for instance. In another embodiment, the coupling may also involve a couplant for enhancing the coupling between the transducers 122-$j$ and the elongated test object 100. Indeed, the present invention may be useful when the orientation of each one of the transducers relative to the elongated test object differs from one transducer to another, which may yield uneven transmission and/or reception of acoustic energy with the elongated test object 100. Accordingly, determining the calibration coefficients may be useful even when using a couplant.

As depicted in FIG. 1a, the modules 121-$i$ are distributed at a plurality of circumferential positions around the circumference of the circular cross-section of the elongated test object 100. In an embodiment, a first ring of circumferential distributed transducers can be associated with a first axial position where first received signals are measured, and that a second ring of corresponding circumferentially distributed transducers can be associated with a second axial position where second received signals are measured, wherein the first and the second rings of transducers can be provided in the form of a probe assembly 124, as shown in FIG. 1a. In a preferred embodiment, the probe assembly 124 is provided in the form of a band-like or a belt-like portable probe assembly which may be successively mounted and then dismounted along the elongated test object. Note that FIG. 1a shows the probe assembly 124 when installed on the elongated test object 100 and omits components such as acquisition electronics, computer and software, and user interface, which are schematically depicted in FIG. 1b.

In an embodiment, the probe assembly 124 is configured to both transmit the acoustic signal to the elongated test object 100 and receive a reflected acoustic signal in response to the reflections of the transmitted acoustic signal occurring along the elongated test object 100. This embodiment can be useful in situations where the guided wave inspection instrument is portable and is used to pin point areas of concern along the elongated test object, for instance. In another embodiment, the probe assembly 124 is configured to receive an acoustic signal in response to the propagation of a guided wave acoustic signal transmitted from a remote transmitter located at a distant axial position along the elongated test object 100. This specific embodiment can be useful where the remote transmitter is made integral to the elongated test object 100 and wherein the probe assembly 124 is used solely for reception at different axial positions along the elongated test object 100, for instance.

Figure 1B:
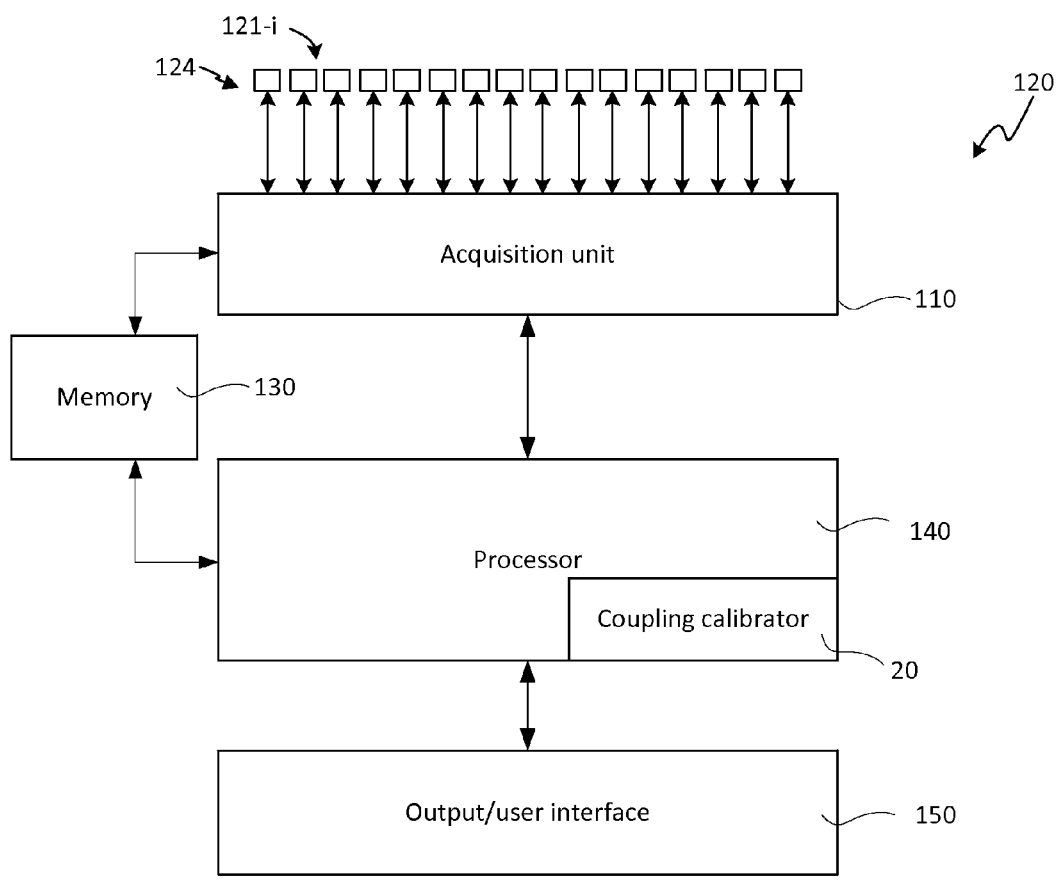
FIG. 1b is a schematic view of the guided wave inspection instrument, in accordance with one embodiment.
Figure 1C:
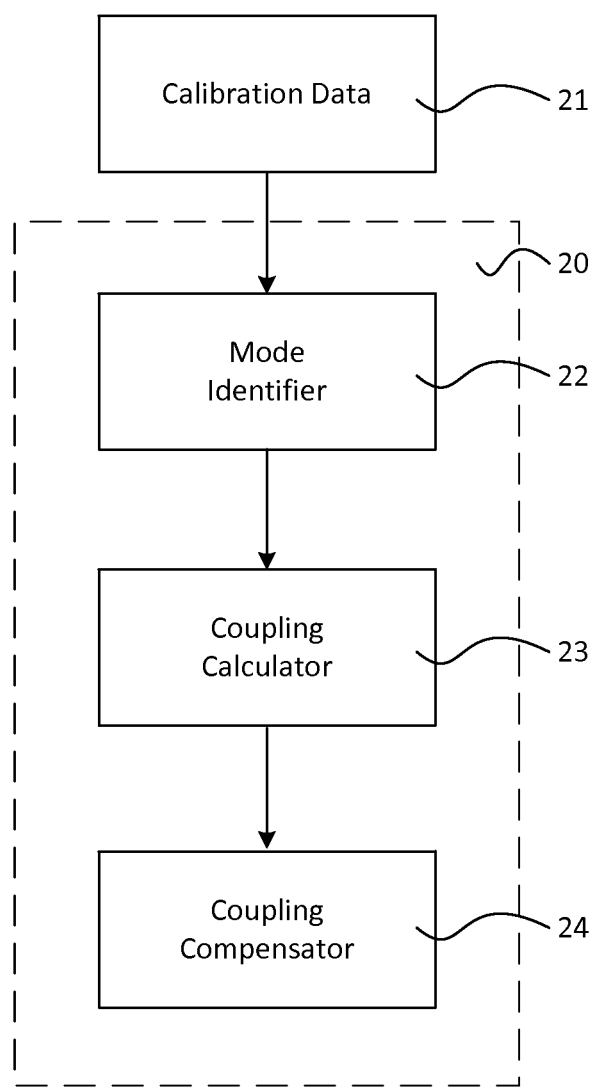
FIG. 1c is the schematic view of the guided wave inspection instrument, in accordance with one embodiment.

FIG. 1*b* shows a schematic view of the guided wave inspection instrument 120. In this specific embodiment, the inspection instrument 120 has modules 121-*i*, an acquisition unit 110, a memory 130, a processor 140, and an output 150, which are coupled from one another. The processor 140 comprises a coupling calibrator 20, which, in turn, comprises a mode identifier 22, a coupling calculator 23 and a coupling compensator 24, as schematically shown in FIG. 1*c*. This schematic view emphasizes the use of the invention from the perspective of the inspection process and does not detail the calibration process itself. The invention takes the form of the coupling calibrator 20 affecting the data acquisition at the transmission stage and/or at the reception stage using the acquisition unit 110 respectively. The probe assembly 124 measures received signal associated with an acoustic mode propagating toward the inspection instrument 120 in the elongated test object. The measured received signal can be stored on the memory 130. The coupling calibrator 20 is adapted to process the measured received signal in order to determine the coupling coefficients with which the inspection instrument 120 is calibrated.

The acoustic mode is known to have a constant amplitude at each one of the circumferential positions of the modules 121-*i*. For instance, the acoustic mode can be the torsional mode $T(0,1)$ which is known to have a constant amplitude along its entire circumference. Moreover, the acoustic mode $T(0,1)$ is known to have a constant phase velocity across a broad range of frequencies. This constant phase velocity allows the coupling calibrator 20 to recognize the acoustic mode using at least two transducers positioned at two distinct axial positions along the elongated test object 100. Indeed, based on the velocity of the guided mode, it is possible to determine the acoustic mode by using a known period of time which depends on the known velocity and the distance d (see FIG. 3*a*) which the acoustic mode has to propagate between the two distinct axial positions. By monitoring the guided mode at each one of the plurality of circumferential positions around the circumference of the elongated test object 100, the calibration coefficients can be calculated in a straightforward manner considering that the amplitude of the monitored guided mode should be constant at each of the circumferential positions around the elongated test object 100. Once determined, the coupling calibrator 20 can calibrate the inspection instrument 120 by supplying the calibration coefficients to the acquisition unit 110 in order to electronically modify the driving voltage and/or the reception gains associated with each one of the modules 121-*i* according to the calibration coefficients. In another embodiment, the coupling calibrator 20 can supply the calibration coefficients to the acquisition unit 110 to modify the compensation gain of each one of the modules 121-*i* according to the calibration coefficients. As mentioned above, using the calibration coefficients only at the reception stage may be useful when the modules are used solely for receiving an acoustic signal which is transmitted from a remote distance along the elongated test object 100. In another embodiment, the calibration coefficients may be used at both the transmission stage and at the reception stage using the acquisition unit 110. In this specific embodiment, the coupling calibrator 20 can be used in an iterative manner so that each detected acoustic signal of the acoustic mode can be used to readjust the calibration coefficients over time. In another embodiment, the coupling calibrator 20 is not physically included in the guided wave inspection instrument 120 and can communicate the calibration coefficients to the acquisition unit 110 using either wired or wireless communication means, for instance.

It is contemplated that the calibration coefficients can be determined individually for each one of the acoustic transducers 122-*j*, or collectively for one group 123-*p*-*j* of acoustic transducers, for instance. Indeed, in an embodiment, the coupling calibrator 20 uses the calibration coefficients to calibrate the inspection instrument 120, and indirectly, each one of the acoustic transducers 122-*j*, based on individually corresponding calibration coefficients. In another embodiment, however, it may be useful to calibrate the inspection instrument 120 with respect to each group 123-*p*-*j* of acoustic transducers using the same calibration coefficients, as will be further described in FIG. 3*b* and FIG. 4.

Still referring to FIG. 1*b*, once the acquisition unit 110 successfully receive the acoustic signal, signal data is transferred to the processor 140 which includes various sub-modules that are needed to provide adequate localization of structural defects along the pipe axis, and possibly, the circumference. Note that it is assumed in this context that the transmission and reception electronics are calibrated and reciprocal, or that the acquisition unit 110 are designed in a way that the coupling coefficients retrieved by the coupling calibrator 20 may be applied to the transmission stage and/or to the reception stage. This may allow adequate compensation on both driving voltage and reception gain. For instance, the output 150 can be used for displaying the measured signals to an operator, or can be used for displaying structural defects in a suitable manner according to the industry standards.

FIG. 1*c* is a schematic diagram of the coupling calibrator 20. The workflow involved with the coupling calibrator 20 is run only once per stable mechanical installation of the probe assembly 124. This means that one has to redo the calibration process if nominal installation parameters change. In an embodiment, once the probe assembly 124 is properly seated on the circular cross-section of the elongated test object 100 to be inspected, calibration data 21 comprising measured acoustic signal data is obtained. The calibration data 21 may be indicative of acoustic signals measured at a plurality of different central frequencies and at a corresponding plurality of frequency bandwidths. The time interval over which the calibration data 21 is acquired is such that it excludes the transitory signal features associated with the transmission event (i.e. the "main bang") and short range non-propagating mode features located near the transitory signal features. In a preferred embodiment, the calibration data is obtained by simultaneously pulsing all transducers of a given ring at the prescribed central frequency. Another embodiment would use wave cancelation schemes between multiple rings of transducers to emit a directional guided wave. The acquisition of the calibration data 21 is completed over multiple transmission frequencies.

Still referring to FIG. 1*c*, the calibration data 21 is transferred to the coupling calibrator 20 where it is first analyzed by the mode identifier 22. This mode identifier 22 outputs the calibration data 21 having a maximized $T(0,1)$ acoustic mode. Details regarding the processes included in the mode identifier 22 are presented herebelow in the description of FIGS. 3*a* and 3*b*. The coupling calculator 23 then computes the relative coupling from one group 123-*p*-*j* of acoustic transducer to another in order to determine the calibration coefficients. The coupling calculator 23 may include time averaging techniques to deduce coupling coefficients. These coupling coefficients may be obtained for multiple transmission frequencies, in which case the inspections at the corresponding frequencies may be calibrated with associated compensation coefficients. Still referring to FIG. 1c, once the coupling coefficients are computed, they are transmitted to the coupling compensator 24 which, accordingly, calibrates compensating gain factors in reception and compensating voltage correction factors for all analyzed transducer 122-j, possibly over multiple transmission frequencies. The coupling compensator 24 stores the compensation coefficients computed from the calibration data and uses them in subsequent normal inspection acquisition schemes. The coupling compensator 24 may be the only sub-module of the coupling calibrator 20 that is actually used in the normal inspection process depicted in FIG. 1b.

Figure 2:
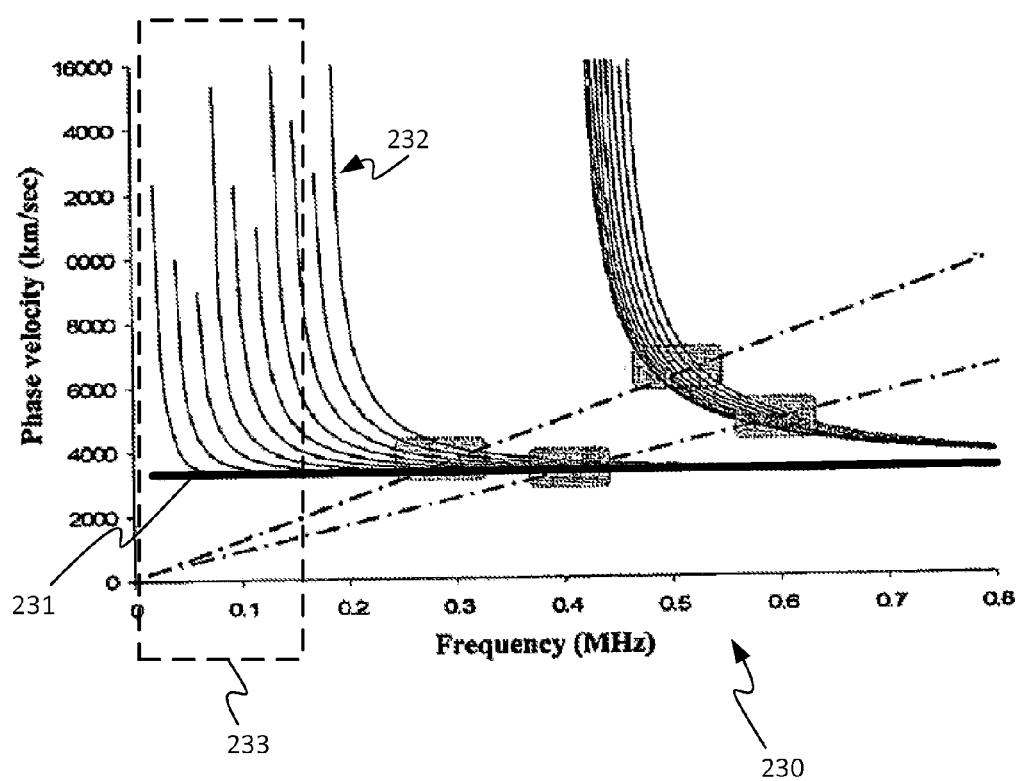
FIG. 2 is a graph showing guided modes dispersion as a function of frequency.

FIG. 2 presents a typical modal phase velocity dispersion plot with respect to frequencies 230. Indeed, the invention makes use of the first torsional mode properties, commonly referred to as T(0,1) mode, in order to successfully compute calibration coefficients both in reception and in transmission. This mode has a uniform acoustic amplitude distribution over the circumference of the test object 100 which makes it a good reference signal in regards to local coupling calibration. Furthermore, its predictable non dispersive behavior eases its detection, as briefly discussed above. The chart shown in FIG. 2 may be drawn from the physical characteristics of the elongated test object of interest including geometry (diameter and wall thickness) and constitutive material(s). Of all modes that exist in a given test object 100 (see for instance one family of dispersion curves 232, each individual curve representing the phase velocity of a given mode with respect to frequency), only the T(0,1) identified by 231 in FIG. 2 has a constant phase velocity. In the case of a simple hollow cylinder, the phase velocity of the T(0,1) mode corresponds to the shear wave velocity of the bulk material of the test object 100, for instance. The asymptotic limit regime of a given dispersive mode descending toward the T(0,1) constant phase velocity may be identified by considering a broad frequency bandwidth 233 of interest. It is based on the insights of this observation, one of the novel aspects of the present disclosure is herein derived as described below.

Figure 3A:
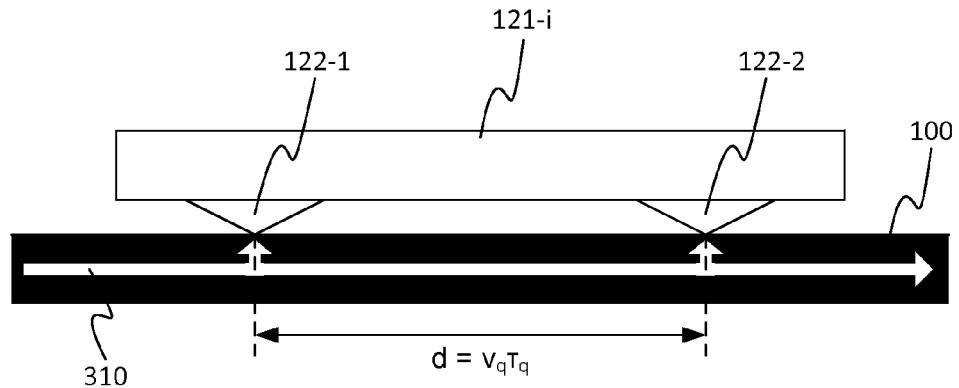
FIG. 3a is a schematic view of an example of an axial cross section of a single module and the corresponding section of an elongated test object, in accordance with one embodiment.

FIG. 3a presents a longitudinal cross sectional view of a module 121-i in contact with the elongated test object 100. Indeed, in order to obtain sufficient data to enable one to identify the spectral content associated with the mode T(0,1), the methods and devices described herein rely on at least two contact transducers 122-j per module 121-i. As illustrated in FIG. 3a, two transducers, illustrated at 122-1 and 122-2, measure a circulating acoustic guided wave 310 at two distinct axial positions, wherein the received acoustic signal measured with 122-1 is delayed by the period of time relative to the received acoustic signal measured with 122-2, for instance. Since the two transducers 122-1 and 122-2 are separated by distance d along the axis of the elongated test object 100, the received echo signals and/or pulses are perceived in a delayed fashion. In other words, the transducer 122-1 records a given received signal some time before the transducer 122-2 does. Because multiple modes coexist at a given frequency, and since these modes possess a wide range of propagation velocities, the recorded period of time between transducers 122-1 and 122-2 of a given pulse associated with the mode q circulating at speed $v_q$ is $\tau_q$. Indeed, the circulating acoustic guided wave 310 is possibly composed of a linear superposition of modes.

Referring to FIGS. 1a and 3a, in one embodiment, the two transducers 122-1 and 122-2 are each aligned axially with corresponding transducers positioned at the other circumferential positions around the test object 100, forming two rings of transducers distributed over multiple groups 123-p-j of transducers, for instance.

Figure 3B:
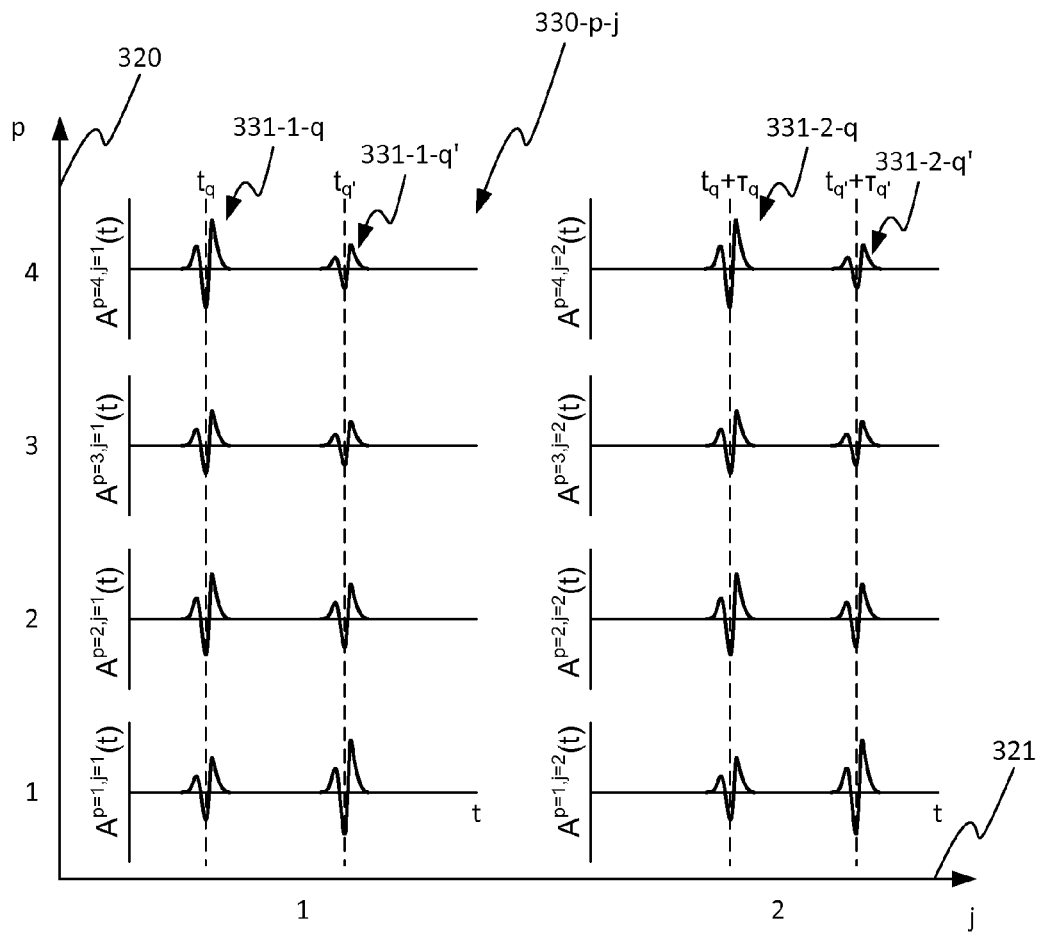
FIG. 3b is a graph showing the acoustic wave time series as perceived by different groups of transducers (abscissa) distributed on four circumferential portions around the elongated test object, in accordance with one embodiment.

FIG. 3b shows an example of the received calibration data 21 comprising RF signals with respect to time that may be displayed in an abstract chart with abscissa 321 representing the transducer rings or ring number (denoted by j), and ordinate 320 representing the different groups 123-p-j of transducers distributed on four circumferential portions around the elongated test object. This identifies a channel (p, j) whose corresponding data set is 330-p-j. Because of the known period of time between reception events of signals associated with the mode T(0,1) as perceived by the two transducers at the two axial positions, the comparison of the data sets corresponding to channels (p, j=1) and (p, j=2) enables one to identify pulses corresponding to mode T(0,1). Essentially, pulsed signals common to both channels, for instance 331-1-q and 331-2-q, and 331-1-q' and 331-2-q' appear delayed by an amount $\tau_q$ and $\tau_{q'}$ corresponding to the velocity of the mode T(0,1), for instance. Pulses delayed by the period of time associated with the mode T(0,1) are thus kept for determining the calibration coefficients for each one of the modules of transducers.

Furthermore, because mode T(0,1) is non-dispersive (i.e. the T(0,1) mode echoes appear at the same time positions on all charts 330-p-j, notwithstanding its frequency), the comparison may also be carried out over the frequency axis using calibration data 21 acquired at different frequencies, for instance. In this specific embodiment, the comparison, which is the main function of the mode identifier 22 in FIG. 1c, may be implemented using a correlation of two channels (p, j=1) and (p, j=2) at two distinct frequencies. Indeed, the elongated test object 100 may be interrogated at a first frequency and at a different, second frequency for correlation thereafter. The resulting measured signals may differ in pulse width, for instance, and may not be comparable in a straightforward manner. In this example, one should scale the time axis with regards to the difference in pulse widths before carrying out the comparison. Once this scaling step is performed, interpolation of the scaled data sets is enabled. The mode identifier 22 presented in FIG. 1c searches for local positive maxima of the correlation signal recurrently appearing at the same time position over multiple transmission frequencies. These identify the T(0,1) related features.

Another comparison scheme may be implemented by summing channel (p, j=1) data and a delayed channel (p, j=2) data according to the T(0,1) expected period of time. Indeed, signal features coherent to both data sets interfere constructively, while incoherent signal features sum up at a lower average amplitude than their individual components (i.e. the interference is partly destructive). Improved statistics may be obtained by assessing the acoustic mode at multiple frequencies.

The chosen comparison scheme may also include pre-processing steps for signal features extraction from all channels (p, j) of a given ring j using Principal Component Analysis (PCA) and Independent Component Analysis (ICA). The chosen comparison scheme may be carried out based on the main features of the signal.

Once the T(0,1) mode related features are isolated using the acoustic signals measured using the modules groups p at each one of the circumferentially positions either using correlation of the received signals or summation of the received signals, the calibration coefficients can be determined and used for calibrating the inspection instrument 120. As mentioned above, in an embodiment, the correlation of the received signal involves correlating signals associated with the transducers of one ring with the signals associated with the transducers of the other ring while using the T(0,1) period of time depending on the distance d between the two rings. In another embodiment, the received signals are summed, using the T(0,1) period of time, which can enhance the amplitude of coherent features of the acoustic mode FIG. 4 shows a schematic transversal cross-sectional view of the test object 100 having the modules 121-*i* disposed on an exterior surface of the test object 100. As shown, the T(0,1) mode feature is schematically represented in FIG. 4 where a cross section of the elongated test object 100 is shown along with representations of isolated T(0,1) mode circulating field amplitude or correlation level 430-*p* for each group 123-*p-j* (for the sake of clarity, a single transducer per group is depicted for each one of the eight groups depicted) covering a given circumferential portion 401-*p*, and perceived field amplitude or correlation level 432-*p* that is recorded for all transducer groups 123-*p-j* at a given time. Essentially, the process using the T(0,1) mode period of time between the two transducers to identify the T(0,1) mode related features along the time series of each group 123-*p-j* has enabled us to factor out an amplitude or correlation level (depending on the preferred method) corresponding to the T(0,1) mode irrespective of the relative signal size from one group p to another. In other words, by carrying out the comparison scheme as presented above, one isolates the T(0,1) acoustic mode without relying on the relative recorded amplitude from one group 123-*p-j* of transducer to another. Since the T(0,1) mode is known to possess uniform acoustic amplitude 430-*p* at a given time position when the measurements are done at given axial positions (see the probe assembly 124 depicted at FIG. 1*a*), one computes a ratio of the perceived amplitude or correlation level 432-*p* at using the period of time for all groups 123-*p-j* of transducers with the corresponding maximum registered value at a given time for all groups 123-*p-j*. The ratio computed establishes the relative coupling level 431-*p* (or square of it if the correlation measurement is used) between the circulating T(0,1) mode acoustic amplitude and the measured amplitude for all groups 123-*p-j* of transducers.

Since relative coupling coefficients from one group p to the maximum amplitude group are obtained for all groups for many time positions, one may compute averages on the relative calibration coefficients for each group p in fashions described in U.S. Pat. No. 9,577,629 and US 2013/0194891. Furthermore, one may reject from the averaging process coupling coefficients corresponding to low signal strengths. Avoiding to do so would include low amplitude noise related to calibration coefficients in the final averaged calibration coefficients hence strongly changing the calibration coefficients although, in principle, they should remain stable over time.

The averaged calibration coefficients are passed to the coupling compensator 24 shown in FIG. 1*c*, so that driving voltage and/or reception gains are equalized over the circumference of the test object 100. The voltage and/or gain compensation factors may be applied for all subsequent inspection runs until the probe assembly 124 is dismounted from the pipe or the calibration nominal parameters are lost.

FIG. 5 shows one exemplary method 500 for inspecting a test object 100 using the methods and devices described herein. Indeed, the method 500 includes installing the probe assembly 124 of the guided wave inspection instrument 120 on the test object 100 to be inspected at 501, measuring the received signals resulting from the propagation of an acoustic guided wave signal along the elongated test object for each of the channels using the acquisition unit 110 at 502, identifying the acoustic mode (e.g. the T(0,1) mode) in the measured acoustic signals using a period of time for each of the channels using the mode identifier 22 at 503, determining a coupling coefficient associated with the acoustic mode for each of the channels using the coupling calculator 23 at 504, which defines compensation factors both in transmission voltage and/or reception gain used for the step of calibrating the inspection instrument 120 using the coupling compensator 24 at 505. As mentioned above, each of the steps 503, 504 and 505 is performed by the coupling calibrator 20 of the processor 140 illustrated in FIG. 1*b*, and more particularly by a corresponding one of the mode identifier 22, the coupling calculator 23 and the coupling compensator 24 depicted in association with FIG. 1*c*. The compensation factors are then used throughout the normal inspection phase until the inspection is completed or nominal installation parameters are changed at 506. It is understood that the step 505 of calibrating the inspection instrument 120 is to be performed electronically via the coupling calibrator 20. Indeed, the acquisition unit 110 are adapted to electronically modify the driving voltages and/or the reception gains associated with each one of the transducers 122-*j*, or group of transducers, upon reception of corresponding instructions from the coupling calibrator 20 based on the calibration coefficients.

As can be understood, the examples described above and illustrated are intended to be exemplary only. For instance, the coupling calibrator 20 can be physically separate from the processor 140 whereby the coupling calibrator 20 is coupled to the processor 140 via a wired or a wireless manner. The scope is indicated by the appended.

What is claimed is:

1. A method for calibrating an inspection instrument coupled with a plurality of acoustic transducers disposed at a plurality of circumferential positions distributed on a test surface of an elongated test object to be inspected, each of the acoustic transducers is acoustically coupled with the test surface during operation, the method comprising the steps of:

for each one or one group of the plurality of circumferential positions,
        measuring at least a first and a second received signal using at least two or two groups of acoustic transducers disposed at two distinct axial positions along the elongated test object, the received signals resulting from the propagation of an acoustic guided wave signal along the elongated test object;
        identifying an acoustic mode according to the first received and the second received signals using a known period of time associated with the propagation of the acoustic guided wave signal between the two axial positions along the elongated test object; and
        determining a coupling coefficient associated with the acoustic mode, the coupling coefficient being indicative of the relative coupling condition between at least one of the at least two or two groups acoustic transducers and the elongated test object; and,
    calibrating the inspection instrument for the at least one of the at least two or two groups of acoustic transducers based on the plurality of coupling coefficients.

2. The method of claim 1, wherein the identified acoustic mode is a T(0,1) mode and has an amplitude uniform across the circumference of the test surface of the elongated test object.

3. The method of claim 1, wherein said calibrating includes modifying driving voltages associated with each one of the plurality of transducers based on the determined calibration coefficients.

4. The method of claim 1, wherein said calibrating includes modifying reception gains associated with each one of the plurality of transducers based on the determined calibration coefficients.

5. The method of claim 1, wherein the first and the second received signal are measured at a plurality of central frequencies and across a corresponding plurality of bandwidths, wherein said obtaining, said identifying, said determining and said calibrating are performed for each one of the plurality of bandwidths.

6. The method of claim 1, wherein the coupling coefficient associated with a circumferential position is an average of the coupling coefficients determined using each one of the at least two transducers at the circumferential position.

7. The method of claim 1, wherein said identifying includes correlating the first acoustic signal data to the second acoustic signal data, wherein said identifying is based on the known period of time.

8. The method of claim 1, wherein said identifying includes shifting one of the first and the second acoustic signal data by the known period of time and summating the shifted acoustic signal data to the other one of the first and the second acoustic signal data, wherein said identifying is based on a maximum of said summating.

9. The method of claim 1, wherein said measuring includes transmitting an acoustic signal along the elongated test object using the plurality of transducers and wherein the first and the second received acoustic signals are reflected acoustic signals resulting from the reflection of the transmitted acoustic signal propagating along the elongated test object.

10. The method of claim 9, wherein said transmitting is performed using the plurality of transducers at both the two axial positions such that the transmitted acoustic signal is directed to only one direction along the elongated test object.

11. A coupling calibrator for calibrating an inspection instrument coupled with a plurality of acoustic transducers disposed at a plurality of circumferential positions distributed on a test surface of an elongated test object to be inspected, each of the acoustic transducers is acoustically coupled with the test surface during operation, the coupling calibrator comprising:
a mode identifier configured to, for each one or one group of the plurality of circumferential positions,
obtain at least a first and a second received signal being measured using at least two or two groups of acoustic transducers disposed at two distinct axial positions along the elongated test object, the received signals resulting from the propagation of an acoustic guided wave signal along the elongated test object; and
identify an acoustic mode according to the first received and the second received signals using a known period of time associated with the propagation of the acoustic guided wave signal between the two axial positions along the elongated test object;
a coupling calculator configured to determine a coupling coefficient associated with the acoustic mode for each one of the one or the one group of the plurality of circumferential positions, each of the coupling coefficients being indicative of the relative coupling condition between at least one of the two or the two groups of acoustic transducers and the elongated test object; and
a coupling compensator configured to calibrate the inspection instrument for the at least one of the two or the two groups of acoustic transducers based on the plurality of coupling coefficients.

12. The coupling calibrator of claim 11, wherein the identified acoustic mode is a T(0,1) mode and has an amplitude uniform across the circumference of the circular test surface of the elongated test object.

13. The coupling calibrator of claim 11, wherein the coupling compensator is configured to modify driving voltages associated with each one of the plurality of transducers based on the determined calibration coefficients.

14. The coupling calibrator of claim 11, wherein the coupling compensator is configured to modify reception gains associated with each one of the plurality of transducers based on the determined calibration coefficients.

15. The coupling calibrator of claim 11, wherein mode identifier is configured to identify the acoustic mode at a plurality of central frequencies and across a corresponding plurality of bandwidths, wherein the coupling calculator determines calibration coefficients for each one of the plurality of bandwidths.

16. The coupling calibrator of claim 11, wherein the coupling calculator is configured to average the coupling coefficients associated with a circumferential position.

17. The coupling calibrator of claim 11, wherein the mode identifier is configured to correlate the first acoustic signal data to the second acoustic signal data, and wherein said identifying is based on the known period of time.

18. The coupling calibrator of claim 11, wherein the mode identifier is configured to shift one of the first and the second acoustic signal data by the known period of time and to sum the shifted acoustic signal data to the other one of the first and the second acoustic signal data, and wherein said identifying is based on a maximum of said summation.

19. A guided wave inspection instrument for inspecting an elongated test object, the guided wave inspection instrument comprising:
a probe assembly coupled with a plurality of acoustic transducers to be disposed at a plurality of circumferential positions distributed on a test surface of the elongated test object to be inspected, each of the acoustic transducers is acoustically coupled with the test surface during operation;
an acquisition unit for receiving at least a first and a second received signal using at least two or two groups of acoustic transducers disposed at two distinct axial positions along the elongated test object, the received signals resulting from the propagation of an acoustic guided wave signal along the elongated test object;
a memory for storing calibration data comprising the received signals;
a processor coupled to the acquisition unit and to the memory, the processor further comprising
a mode identifier configured to, for each one or one group of the plurality of circumferential positions,
obtain at least a first and a second received signal being measured using at least two or two groups of acoustic transducers disposed at two distinct axial positions along the elongated test object, the received signals resulting from the propagation of an acoustic guided wave signal along the elongated test object; and identify an acoustic mode according to the first received and the second received signals using a known period of time associated with the propagation of the acoustic guided wave signal between the two axial positions along the elongated test object;

a coupling calculator configured to determine a coupling coefficient associated with the acoustic mode for each one of the one or the one group of the plurality of circumferential positions, each of the coupling coefficients being indicative of the relative coupling condition between at least one of the two or the two groups of the plurality of the acoustic transducers and the elongated test object; and a coupling compensator configured to calibrate the guided wave inspection instrument for the at least one of the two or the two groups of acoustic transducers based on the plurality of coupling coefficients.

20. The guided wave inspection instrument of claim 19, wherein the identified acoustic mode is a T(0,1) mode and has an amplitude uniform across the circumference of the test surface of the elongated test object.

* * * * *